(12) United States Patent
Caspers

(10) Patent No.: US 7,150,762 B2
(45) Date of Patent: Dec. 19, 2006

(54) PRESSURE/TEMPERATURE MONITORING DEVICE FOR PROSTHETICS

(75) Inventor: Carl A. Caspers, Avon, MN (US)

(73) Assignee: Otto Bock HealthCare LP, Minneapolis, MN (US)

( * ) Notice: Subject to any disclaimer, the term of this patent is extended or adjusted under 35 U.S.C. 154(b) by 30 days.

(21) Appl. No.: 10/699,720

(22) Filed: Nov. 3, 2003

(65) Prior Publication Data
US 2004/0167638 A1 Aug. 26, 2004

Related U.S. Application Data

(60) Provisional application No. 60/422,965, filed on Nov. 1, 2002.

(51) Int. Cl.
A61F 2/60 (2006.01)
A61F 2/78 (2006.01)

(52) U.S. Cl. ......................... 623/33; 623/912

(58) Field of Classification Search ............ 623/27–37, 623/912
See application file for complete search history.

(56) References Cited

U.S. PATENT DOCUMENTS

| 4,387,472 A * | 6/1983 | Wilson .................... 623/49 |
| 5,253,656 A | 10/1993 | Rincoe et al. |
| 5,888,230 A * | 3/1999 | Helmy .................... 623/34 |
| 6,500,210 B1 * | 12/2002 | Sabolich et al. .......... 623/24 |
| 6,508,842 B1 | 1/2003 | Caspers |
| 2004/0059432 A1 * | 3/2004 | Janusson et al. ......... 623/36 |

FOREIGN PATENT DOCUMENTS

| DE | 40 39 648 | 7/1992 |
| WO | WO 98/04182 | 2/1998 |
| WO | WO 00/74611 | 12/2000 |

OTHER PUBLICATIONS

Wayne J. Board, "Below-knee Amputee Residual Limb Responses to Vacuum-Assisted and Suction Socket Conditions", St. Cloud State Univ., Oct. 2000.
Tracy L. Beil, "Interface Pressures During Ambulation Using Suction and Vacuum-Assist Prosthetic Sockets", St. Cloud State Univ., Jul. 2001.
Robert M. Harvey et al., *Research Forum—Methodology Measurements, Part II: Instrumentation and Apparatus*, Journal of Prosthethics and Orthotics, vol. 8, No. 2, 1996 (pp. 50-64).
Arthur F. T. Mak et al., *State-of-the-art research in lower-limb prosthetic biomechanics—socket interface*, Department of Veterans Affairs Rehabilitation Research & Development Service, vol. 38, No. 2, Apr. 2001.

* cited by examiner

*Primary Examiner*—Bruce Snow
(74) *Attorney, Agent, or Firm*—Faegre & Benson, LLP

(57) ABSTRACT

An apparatus and method for monitoring aspects of a socket of a prosthetic limb having a residual limb contained therein. The apparatus includes and the method uses sensors for measuring one or more of pressure, force, temperature, moisture, and vacuum and one or more devices for displaying sensor values to the wearer, setting sensor limits, and/or sounding an audible alarm when a sensor limit is exceeded.

32 Claims, 3 Drawing Sheets

PRESSURE/TEMPERATURE MONITORING DEVICE FOR PROSTHETICS

This application claims priority to U.S. Provisional Patent Application Ser. No. 60/422,965, filed on Nov. 1, 2002 and entitled PRESSURE/TEMPERATURE MONITORING DEVICE OF PROSTHETICS, which is herein incorporated by reference in its entirety.

BACKGROUND OF THE INVENTION

The present invention relates to an apparatus for monitoring the environment of a prosthetic socket, and in particular to an apparatus for monitoring various parameters such as temperature, pressure, moisture, and vacuum, and for signaling the wearer of the prosthetic limb when one of these parameters exceeds a pre-set range.

A study conducted under direction of the Applicant/Inventor by Wayne J. Board in partial fulfillment for a Masters degree has shown that application of a vacuum on the expulsion port of a total surface-bearing socket to hold the liner tightly against the socket can prevent loss of residual limb volume due to ambulation, and can in fact result in an increase in residual limb volume. Wayne J. Board, "Below-knee Amputee Residual Limb Responses to Vacuum-assisted and Suction Socket Conditions", St. Cloud State Univ., October, 2000.

A second study, also conducted under the direction of the Applicant/Inventor in partial fulfillment for a Masters degree has shown that interface pressures, measured at five points between the surface of the residual limb and the liner, were quite different between a standard total surface-bearing socket and a vacuum-assisted socket. Tracy L. Beil, "Interface Pressures During Ambulation using Suction and Vacuum-assisted Prosthetic Sockets", St. Cloud State Univ., July, 2001. The vacuum-assisted socket created significantly lower positive impulse and peak pressures during the stance phase of ambulation. Ibid. The impulse, average, and peak negative pressure values calculated for the swing phase of ambulation were significantly greater in magnitude with the vacuum-assisted socket. Ibid. It is thought that lower pressures seen during both stance and swing phases using the vacuum-assisted socket reduce the fluid forced out and increase the amount of fluid drawn into the limb, thereby preventing volume loss. Ibid.

Previous to the above two studies, the present inventor disclosed, in application Ser. No. 09/492,406 (now issued U.S. Pat. No. 6,508,842 and herein incorporated by reference), that application of vacuum to an artificial limb socket can prevent the loss of residual limb volume.

Ambulation causes the shape of the residual limb, the temperature within the prosthetic socket, and pressures within the socket to change. There is a need for a device to warn the patient that certain levels have been exceeded.

SUMMARY OF THE INVENTION

An apparatus for one or more aspects relating to a socket of an prosthetic limb having a residual limb contained therein. The apparatus can include at least one of a pressure sensor and a force sensor, a temperature sensor, a moisture sensor, a vacuum sensor, a display of values sensed by at least one of these sensors, and an alarm for indicating when a value sensed by one of these sensors is beyond a sensor value limit.

One embodiment of the present invention could involve warning the patient when the vacuum, i.e. lowered pressure, between the liner or limb and the socket is lost or being lost. The patient may then take some action to restore or adjust this vacuum, such as changing a setting on a vacuum pump, walking faster (in the case of a weight-actuated vacuum pump), or checking the seal between the residual limb and the socket.

Another embodiment of the present invention could involve warning the patient when the temperature within the socket exceeds a certain level or falls outside a range. This can occur when the vacuum breaks down. It may also be a symptom of inflammation in the residual limb or of loss of blood circulation.

Another embodiment of the present invention can involve monitoring pressures between the liner and the socket and between the liner and the skin and warns the patient if these pressure changes differ significantly from preset levels. This may indicate a misfitted socket.

Another embodiment of the present invention can involve monitoring moisture within the socket and warning the patient if the moisture level differs significantly from preset levels. It is known that too much moisture, due to perspiration, may adversely affect the fit and performance of the socket.

Another embodiment is an apparatus for monitoring the environment of the prosthetic socket of an artificial limb having a residual limb contained therein. The apparatus can include at least one sensor for sensing at least one of pressure, force, temperature, and moisture, wherein the at least one sensor can be configured with value limits. The apparatus can also include an alarm when a value sensed by the at least one sensor is beyond a value limit.

Another embodiment of the present invention is a method for monitoring one or more aspects relating to a socket of a prosthetic limb and a residual limb contained therein. This method can include sensing at least one of pressure, force, temperature, and moisture with respect to at least one the socket, the artificial limb, and a space therebetween. It can also include setting sensor value limits, and indicating when a sensed value is beyond at least one of the sensor value limits.

DETAILED DESCRIPTION OF THE PREFERRED EMBODIMENT

Measurement of Pressure

The present invention may be used to measure the following pressures: negative pressure between the socket and the liner; negative pressure between the liner and the skin of the residual limb; positive pressure between the liner and the socket; and positive pressure between the liner and the skin.

Methods and instrumentation used to measure pressure have been previously described. Beil, 2001. The following is a discussion of this methodology as discussed in Beil.

Pilot Testing

Extensive pilot work, primarily on the force sensing resistors, was completed prior to conducting the current study. By working with the sensors, the limitations were noted and procedures were created to achieve the most reliable results. Several researchers have reported on this type of sensor's performance in regards to shear forces, hysteresis, temperature and response to dynamic loading. Jensen (1991) found that shear forces did not cause a systemic error in the output of the force sensing resistors to compressive pressures. Hysteresis was found to significantly raise sensor output during unloading, but calibrating at a temperature of 99° F. did not significantly differ from that at a temperature of 69° (Hachisuka, 1998). These sensors also were noted to have good dynamic response to pressures applied in a cyclic fashion at 1 or 2 Hz (Buis, 1997; Jensen, 1991).

Sensor Preparation. In order to function properly, a small vent hole on the sensor had to be exposed to atmospheric pressure, which was quite difficult since the sensors were exposed to liquid urethane during the pouring of the urethane liner. Venting was accomplished by running a tube from the sensor through the liner wall out to the atmosphere. An airtight system was created for each sensor by following a few procedures. Cloth tape was placed on the back of the sensor tail to create an air wick from the sensor vent hole to the tubing that contains the wires at the solder tabs. Two pieces of electrical tape enclosed the sensor from the active area to the tubing and were completely sealed by painting liquid electrical tape around the edges of the regular electrical tape. Success of the process was checked by monitoring the resistance of the sensor while air was drawn through the tube. When the system was sealed, the initial infinite resistance dropped to approximately 1500 ohms. If the resistance did not drop immediately, the system was not sealed and could not be placed into a liner during pouring. The urethane would leak into the sensor resulting in inaccurate measurements.

Figure 1:
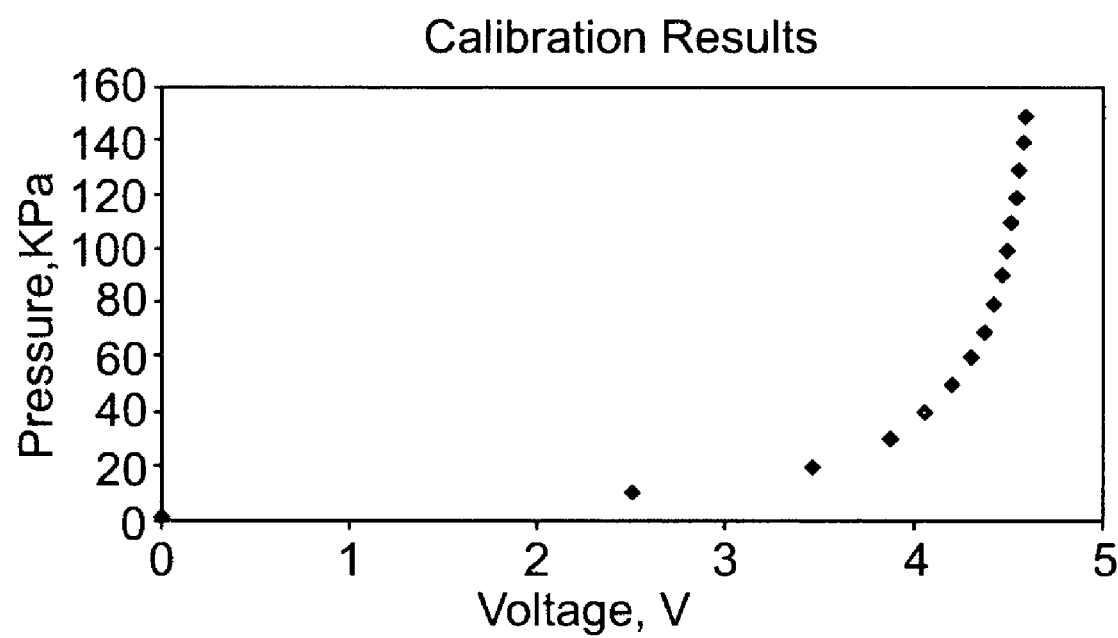
FIG. 1 is a graph showing sensor calibration.

Calibration. The calibration procedures during the pilot work were performed using a blood pressure cuff contained in a wooden box. Pressure was applied with the blood pressure cuff onto a sensor that was placed upon a flat piece of urethane, while the output voltages were simultaneously recorded. The voltages were plotted against the known pressures as in FIG. 1. The shape of the plot was not accurately fitted with a single curve, thus two equations were necessary. An exponential equation was used to fit the voltages from 0 to 30 kPa while a fourth power equation was fit to the rest of the voltages.

Curvilinear results were obtained that proved to be repeatable. Voltages were within 3% at the low pressures and 0.5% at the pressures above 80 kPa. The output from consecutive calibration trials was not found to be significantly different. The curvilinear output of the sensors means that the precision decreases as the pressure increases as can be seen in Table 1. The precision was calculated by dividing the average residual of the regression by the change in voltage per kPa at that point in the calibration curve. A precision of ±0.2 kPa means that the pressure applied can be predicted using the output voltages within ±0.2 kPa. Clearly, the prediction range widens as the applied pressure increases, thus precision is reduced.

TABLE 1

The applied pressures, voltage outputs and precision of the force sensing resistors during calibration.

| Pressure, kPa | Predicted vdc | Precision kPa |
|---|---|---|
| 15 | 2.7531 | |
| 20 | 3.1951 | ±0.2 |
| 25 | 3.4992 | ±0.3 |
| 30 | 3.7065 | ±0.4 |
| 35 | 3.8488 | ±0.6 |
| 40 | 3.9499 | ±0.8 |
| 45 | 4.0268 | ±1.1 |
| 50 | 4.0907 | ±1.3 |
| 55 | 4.1479 | ±1.4 |
| 60 | 4.2012 | ±1.5 |
| 65 | 4.2507 | ±1.6 |
| 70 | 4.2952 | ±1.8 |
| 75 | 4.3330 | ±2.2 |
| 80 | 4.3630 | ±2.7 |

Figure 2:
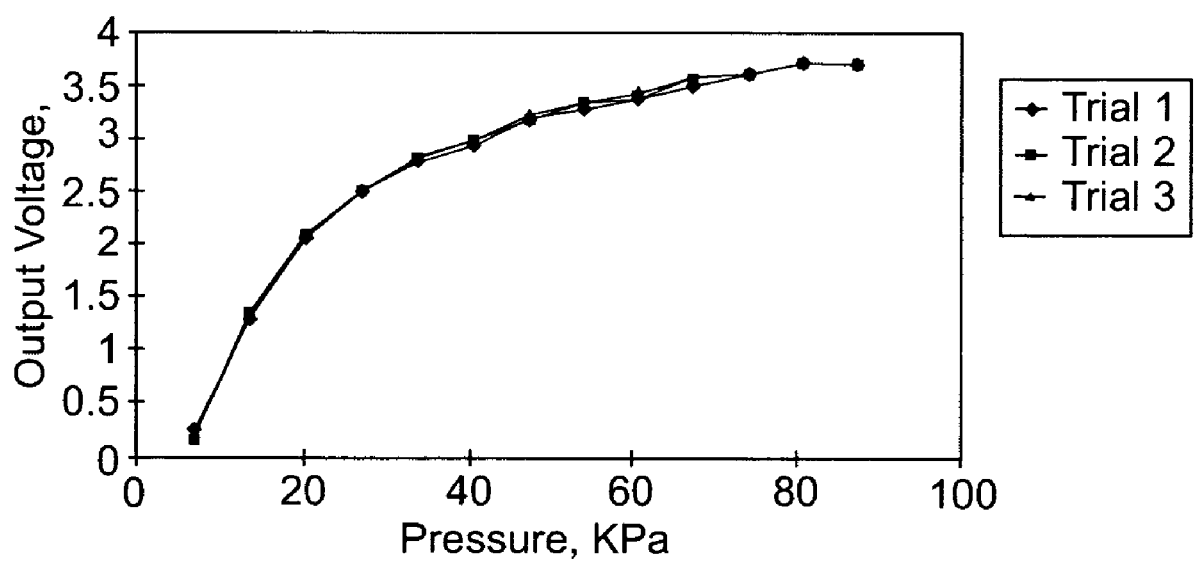
FIG. 2 is a graph showing sensor calibration.
Figure 4:
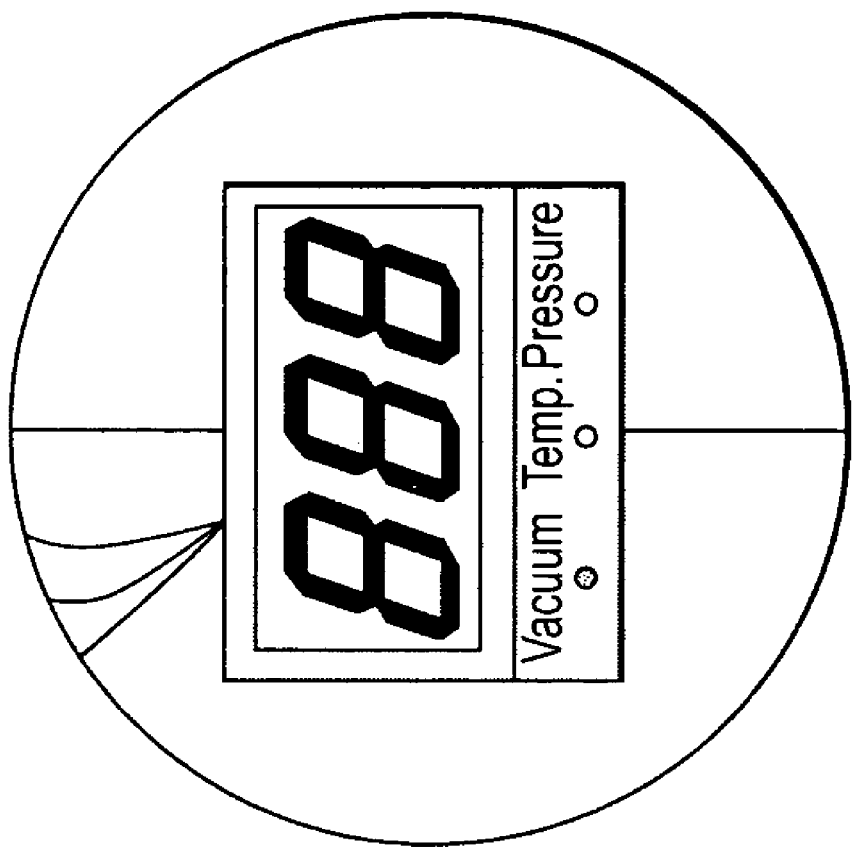
FIG. 4 is a schematic elevational view of a readout device for displaying various parameters to the patient.
Figure 3:
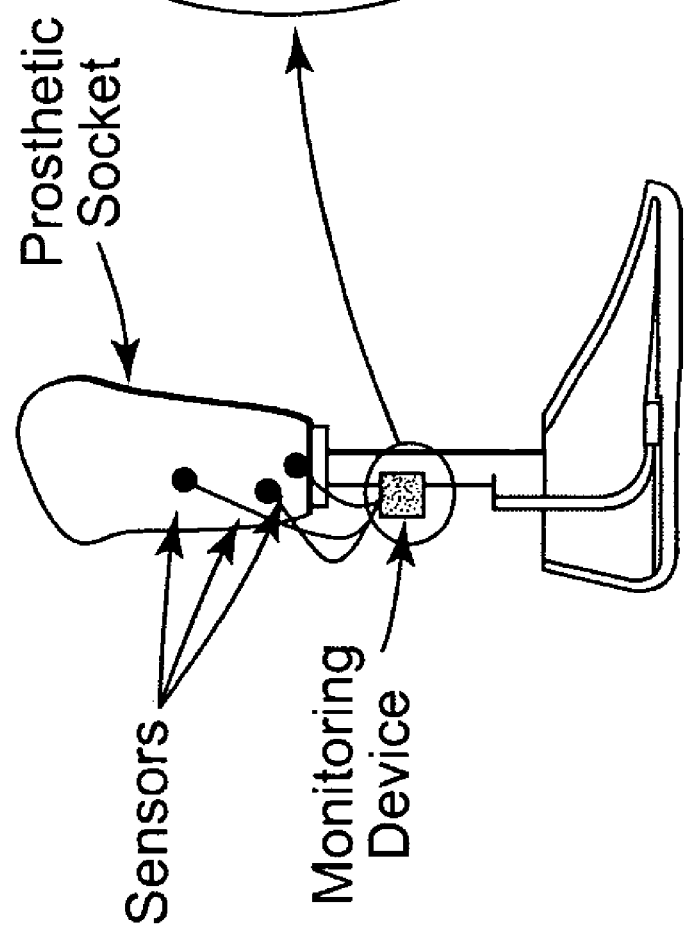
FIG. 3 is a schematic side elevational view of an artificial limb with a monitoring device and various sensors.

Socket condition testing. The socket environment exposed the sensors to curvature and elevated temperature due to contact with the residual limb. Calibration procedures were performed with the sensor on a 76 mm curvature, which was representative of the residual limb size of the subjects that participated in this study. The calibration curve was found to maintain its shape and repeatability as is shown in FIG. 2.

Calibration was also performed while the sensor was at 98–100° F. and the electronics were at room temperature. The output voltages increased by 0.18 vdc/° F.[1]. Care was taken during testing to give the sensors time to reach an equilibrium temperature before pressure measurements are taken.

The performance of the force sensing resistors was found to be acceptable to compare the pressures under the two conditions even if there is error in the absolute pressures measured. The repeatability and precision measurements are within +5%. Errors introduced in the pressure values by hysteresis, increased temperature and curvature will create the same error in both conditions. By taking steps to minimize the errors and understanding the limitations of the sensors, it was felt that these sensors could be used to make comparisons between two conditions when tested in random order and within minutes of each other.

Subject Selection

Nine unilateral below-knee amputees participated in the study. No vascular amputees were included in this study. Since the study compared measurements made during walking, all subjects regularly used a total surface-bearing socket and walked daily.

Apparatuses

Prosthetic System. One prosthetic system was used for each subject during the study. It included a traditional total surface-bearing socket with a one-way check valve at the distal end. The amputee first donned a urethane liner with a nylon sheath over it. The leg was then placed into the test-socket. A urethane suspension sleeve was rolled over the top half of the socket and the lower thigh to create suspension for the leg. This configuration was also used for the vacuum-assigned condition with the addition of a vacuum pump (Gast) connected to the one-way check valve that drew a vacuum of −69 kPa in the space found between the liner and the socket. The socket was attached to a pylon and a Solid Ankle Cushion Heel (SACH) foot to complete the system.

Liner Instrumentation. Documenting interface pressures between the residual limb and liner or liner and socket had many inherent difficulties. Access to the interface was quite limited, forcing researchers to modify the socket or liner to implement the sensors, thereby compromising the integrity of the results. Two major methods of sensor placement have been used in interface pressure studies. The first method involved placing the sensor in the wall of the socket. A hole was drilled through the socket wall and the sensor was affixed such that it was flush with the inner socket wall or liner (Sanders, 1999; Sanders, 1997; Sanders, 1993; Sanders, 1992; Zhang, 1998). This required modification of the socket and could have influenced the results obtained. This option was not used in this study because it would interfere with the sealed chamber needed between the liner and socket. An alternative option was used in this study in which the sensors were placed between the liner and the skin. In order to successfully accomplish this task, the sensors needed to be as thin as possible and be able to conform to the curved surface of the limb. Five force sensing resistors capable of measuring positive normal forces (Interlink Electronics, Camarillo, Calif. part #402) were placed on the liner mold prior to pouring. The flexible sensors had a thickness of 0.46 mm and 12.7 mm diameter. By having the force sensing resistors in the liner, the sensors were flush with the inner wall of the liner. This was crucial since sensor protrusion can lead to elevated pressure readings (Appoldt, 1969). The wiring of the sensors exited through the liner wall, maintaining the seal between the limb and liner.

Since soft tissues were the most capable of volume loss, the sensor placement avoided bony prominences and areas of soft tissue were targeted. The most proximal sensor was placed on the gastrocnemius below the posterior trim lines of the socket. Medial and lateral sensors were placed at the distal end avoiding the extreme curvature seen at the end of the limb. Two more sensors were placed mid-distance between the proximal and distal sensors. The complete sensor placement formed a pentagon on the posterior side of the residual limb.

A sixth sensor capable of documenting negative air pressures using a full bridge (Endevco, San Juan Capistrano, Calif.) was placed at the distal end of the liner. A 12×8×8 mm piece of Pelite foam was glued to the male liner mold before pouring the liner. This ensured that a cavity of the proper size would exist at the distal end of the liner for placement of the air pressure sensor. The sensor was protected with a casing and cloth to ensure that the sensor was not damaged during weight bearing phases and that the air had access to the sensor at all times. A flat, thin wire from the sensor was anchored at the distal end of the liner and run along the limb out of the liner.

Electronics. The force sensing resistors were part of a voltage dividing circuit with a fixed resistor of 5.1 Kohm. The sensor was powered with 5 vdc and an operational amplifier chip (LM324AN-Digi-Key, Thief River Falls, Minn.) was powered with 6.5 vdc. The air pressure sensor was excited with 10 vdc and run through an operational amplifier (Transducer Techniques, Model M-2). All sensors were fed into a 12-bit A/D board (Keithley Instruments, Cleveland, Ohio) and read on a personal computer.

Calibration. The calibration procedures used for the force sensing resistors have been previously described above. Pressures from 0–150 kPa were twice applied randomly at 10 pKa increments per sensor. Calibration of the air pressure sensor was completed in a sealed tube with a plunger that allowed negative pressures to be applied to the sensor. Pressures ranging from 0 to −80 kPa were applied for calibration. A linear voltage output was attained to which a regression equation was fit.

PROCEDURES

Prosthetic Fitting

Subjects were cast within three months prior to their testing day. This was done to ensure that properly fitting custom made liners and sockets were manufactured for each subject. The time between the casting and testing allowed for instrumentation and calibration of the liners without significant long-term changes in limb volume.

Pressure Measurement

Subjects reported to the laboratory early in the morning to allow as little volume loss as possible before testing. Upon arrival, a registered prosthetic technician aligned the prosthetic leg dynamically. Each subject was comfortable in the new system before testing continued. When donning the liner, any air remaining between the skin and the liner was worked out of the system. Once this was accomplished, Vaseline was placed around the flat wire as it exited the liner to minimize the movement of air along the wire.

Subjects were randomly assigned to begin with the traditional total surface-bearing socket or vacuum-assisted socket condition and alternated conditions until at least three trials of each condition were completed. One 8-second sample at 100 Hz was taken during each trial creating three sets of pressure measurements per condition. Bates (1992) suggested that with ten subjects participating in the study three trials would provide enough statistical power for analysis, but five trials would be ideal.

Measurements were taken while the subject walked on a 20 meter straightaway. A subject's walking velocity was controlled at 4 km/hr by having the subject follow a string controlled by a motor. This speed was the mean of speeds used in gait analysis and energy expenditure studies completed by several researchers on below-knee amputees (Casillas, 1995; Gailey, 1997; Gitter, 1991; Hunter, 1995, Hermodsson, 1994). Care was taken to sample only when the subject was walking at the correct velocity and not in the process of accelerating or decelerating.

Once the data were collected, heelstrike and toe-off were marked for each step by looking at the rate of change in pressure of the distal air pressure sensor. This sensor was quite sensitive to the vertical displacement of the prosthesis at heelstrike and toe-off. The maximum positive and negative slopes were found for each trial. The midpoint of this value was chosen to signify heelstrike and toe-off.

The pressure curves are generally double-peaked during the stance phase and single peaked during the swing phase of ambulation. Peak pressures in stance and swing phases were obtained using a 0.1 second averaging period. Average pressures during stance and swing phase were found using heelstrike and toe-off as the indicators of the beginning and end of the phases. An impulse value was also obtained for stance and swing phases by calculating the area under the respective positive and negative pressure curves. Time of stance and swing phases was also calculated.

Statistical Analysis

Three two-factor repeated measures ANOVAs ($\alpha=0.05$) can be used to determine if there is a difference in the impulse values, average pressure and 0.1 second peak pressures for the five force sensing resistors during stance phase between the two socket conditions. Three single-factor ANOVAs ($\alpha=0.05$) can be run to determine if there is a difference between the two conditions in impulse value, average pressure and 0.1 second peaks of the air pressure sensor during swing phase.

Measurement of Temperature and Moisture

Temperature may be measured by appropriate sensors embedded in the socket wall. Moisture may be measured by an instrument such as a hygrometer.

Interface from Sensors to Monitoring Device

Once the sensors are positioned, the fitter proceeds to set limits (e.g., upper and lower) for the display or alarm, e.g., audible alarm. The display and alarm device preferably uses a digital readout and/or an audible alarm. A schematic of such a device is shown in FIG. 2.

The limits may be set at the device itself or by means of a computer. The computer may be connected to the device by a cable or other means such as an infrared signal.

The patient would then walk for several minutes to establish a baseline and the fitter would then set upper and lower limits based on the information gained.

Once the limits are set, the computer can be disconnected and the device would then operate independently.

The device would monitor temperature (preferably in a range (i.e., within the limits) of 87 to 107 degrees); moisture (relative humidity, preferably in a range from 0% to 100%); pressure (preferably in a range of 0 to 20 psi); and vacuum (preferably in a range of 0 to 28 inches of mercury).

The present invention may be embodied in other specific forms, structures, methodologies, and procedures without departing from the spirit or essential attributes thereof, and it is therefore desired that the present embodiment be considered in all respects as illustrative and not restrictive.

What is claimed is:

1. An apparatus for monitoring one or more aspects relating to a socket of an prosthetic limb having a residual limb contained therein, the apparatus comprising:
   (a) at least one of a pressure sensor and a force sensor;
   (b) a temperature sensor;
   (c) a moisture sensor;
   (d) a display of values sensed by at least one of the pressure sensor, force sensor, temperature sensor, moisture sensor; and
   (e) an alarm for indicating when a value sensed by one of the pressure sensor, force sensor, temperature sensor, and moisture sensor is beyond a sensor value limit.

2. The apparatus of claim 1, further comprising a computer for setting sensor value limits.

3. The apparatus of claim 2, further comprising a disconnectable connection between the computer and the remainder of the apparatus.

4. The apparatus of claim 1, further comprising:
   (f) a liner within the socket; and
   wherein the apparatus is configured such that pressure between the residual limb and the socket or between the socket and the liner can be sensed.

5. An apparatus for monitoring the environment of the prosthetic socket of an artificial limb having a residual limb contained therein, the apparatus comprising:
   (a) at least one sensor positioned at least partially within a wall of the socket for sensing at least one of pressure, force, temperature, and moisture, wherein the at least one sensor can be configured with value limits; and
   (b) an indicator of when a value sensed by the at least one sensor is beyond a value limit; and
   a computer for setting sensor value limits.

6. The apparatus of claim 5 wherein the indicator comprises a display for sensed values.

7. The apparatus of claim 5, further comprising a disconnectable connection between the computer and the remainder of the apparatus.

8. The apparatus of claim 5, further comprising:
   (c) a liner within the socket; and
   wherein the apparatus is configured such that pressure between the residual limb and the socket or between the socket and the liner can be sensed.

9. The apparatus of claim 5, wherein the sensor for sensing pressure can sense a vacuum between the socket and the residual limb.

10. The apparatus of claim 5, wherein the sensor for sensing pressure can sense pressure being applied to a portion of the residual limb.

11. A method for monitoring aspects relating to a socket of a prosthetic limb and a residual limb contained therein, the method comprising:
    (a) sensing at least one of pressure and force, and at least one of temperature and moisture, with respect to at least one of the socket, the residual limb, and a space there between;
    (b) setting sensor value limits; and
    (c) indicating when a sensed value is beyond at least one of the sensor value limits.

12. The method of claim 11, further comprising:
    (d) displaying sensed values.

13. The method of claim 11, wherein the socket includes a liner and wherein sensing pressure comprises sensing a vacuum between the socket and the liner or between the liner and the residual limb.

14. The method of claim 11, wherein sensing pressure comprises sensing pressure being applied to a portion of the residual limb.

15. The method of claim 11, wherein sensing force comprises sensing force being applied to a portion of the residual limb.

16. The method of claim 11, wherein indicating comprises providing an audible alarm.

17. The method of claim 11, wherein sensing temperature comprises sensing temperature within the socket.

18. The method of claim 11, wherein sensing moisture comprises sensing moisture within the socket.

19. The apparatus of claim 5, wherein the indicator comprises an audible alarm.

20. The apparatus of claim 1, further comprising a vacuum sensor, and wherein the display of values is sensed by at least one of the pressure sensor, force sensor, temperature sensor, moisture sensor and vacuum sensor, and wherein the alarm indicates when a value sensed by one of the pressure sensor, force sensor, temperature sensor, moisture sensor and vacuum sensor is beyond a sensor value limit.

21. An apparatus for monitoring the environment of the prosthetic socket of an artificial limb having a residual limb contained therein, the apparatus comprising:
    a liner mountable over the residual limb and having a wall, the liner receivable within the socket;
    at least one sensor positioned within the wall of the liner for sensing at least one of pressure, force, temperature, and moisture, wherein the at least one sensor can be configured with value limits;
    an indicator of when a value sensed by the at least one sensor is beyond a value limit; and
    a computer for setting sensor value limits.

22. The apparatus of claim 21, wherein the indicator comprises a display for sensed values.

23. The apparatus of claim 21, wherein the indicator comprises at least one of an audible alarm and a visual alarm.

24. The apparatus of claim 21, further comprising a disconnectable connection between the computer and the remainder of the apparatus.

25. The apparatus of claim 21, further comprising a sensor for sensing a vacuum within the socket.

26. The apparatus of claim 21, wherein the wall of the liner comprises an inner wall to be positioned adjacent to the residual limb, and wherein the at least one sensor is positioned within the inner wall of the liner.

27. An apparatus for monitoring the environment of the prosthetic socket of an artificial limb having a residual limb contained therein, the apparatus comprising:
(a) at least one sensor positioned within a wall of the socket for sensing at least one of pressure, force, temperature, and moisture, wherein the at least one sensor can be configured with value limits; and
(b) an indicator of when a value sensed by the at least one sensor is beyond a value limit, wherein the indicator comprises an audible alarm.

28. The apparatus of claim 27 further comprising a computer for setting sensor value limits.

29. The apparatus of claim 28, further comprising a disconnectable connection between the computer and the remainder of the apparatus.

30. The apparatus of claim 27, further comprising:
(c) a liner within the socket; and
wherein the apparatus is configured such that pressure between the residual limb and the socket or between the socket and the liner can be sensed.

31. The apparatus of claim 27, wherein the sensor for sensing pressure can sense a vacuum between the socket and the residual limb.

32. The apparatus of claim 27, wherein the sensor for sensing pressure can sense pressure being applied to a portion of the residual limb.

* * * * *